United States Patent [19]
Kotani et al.

[11] Patent Number: 4,872,966
[45] Date of Patent: Oct. 10, 1989

[54] SHEET TYPE ELECTRODE FOR USE IN THE MEASUREMENT OF ION CONCENTRATIONS

[75] Inventors: Haruo Kotani; Katsuhiko Tomita, both of Kyoto, Japan

[73] Assignee: Horiba, Ltd., Kyoto, Japan

[21] Appl. No.: 124,970

[22] Filed: Nov. 24, 1987

[30] Foreign Application Priority Data

Dec. 11, 1986 [JP] Japan ............................ 61-191497[U]

[51] Int. Cl.⁴ ............................................. G01N 27/46
[52] U.S. Cl. .................................. 204/414; 204/416; 204/420; 204/435
[58] Field of Search ............................. 204/416–419, 204/414, 435, 420

[56] References Cited

U.S. PATENT DOCUMENTS

| | | | |
|---|---|---|---|
| 3,250,688 | 5/1966 | Arthur | 204/414 |
| 3,833,495 | 9/1974 | Grubb | 204/195 F |
| 3,911,901 | 10/1975 | Niedrach et al. | 128/2 E |
| 3,957,612 | 5/1976 | Niedrach et al. | 204/195 M |
| 4,053,381 | 10/1977 | Hamblen et al. | 204/195 M |
| 4,105,509 | 8/1978 | Jungck | 204/1 T |
| 4,133,735 | 1/1979 | Afromowitz et al. | 204/195 G |
| 4,180,771 | 12/1979 | Guckel | 204/418 |
| 4,280,889 | 7/1981 | Szonntagh | 204/195 F |
| 4,282,079 | 8/1981 | Chang et al. | 204/195 G |
| 4,454,007 | 6/1984 | Pace | 204/1 T |
| 4,468,271 | 8/1984 | Pierson | 156/220 |
| 4,508,613 | 4/1985 | Busta et al. | 204/419 |
| 4,549,951 | 10/1985 | Knudson et al. | 204/418 |
| 4,592,824 | 6/1986 | Smith et al. | 204/416 |
| 4,636,827 | 1/1987 | Rudolf | 204/418 |
| 4,684,445 | 8/1987 | Seshimoto et al. | 204/416 |
| 4,713,165 | 12/1987 | Conover et al. | 204/418 |

FOREIGN PATENT DOCUMENTS 2541462 8/1984 France .

OTHER PUBLICATIONS

Ser. No. 07/124,909, filed 11/24/87 for "Sheet Type Electrode for Use in Measurement of Ions".
Ser. No. 124,903, filed 11/24/87 for "Reference Electrode".
Ser. No. 1214,567, filed 11/24/87 for "Sheet Type Electrode".
Ser. No. 099,294, filed 9/17/87 for "Gelatinized Member for Use in Electrodes Measuring Ion Concentration".

Primary Examiner—T. Tung
Attorney, Agent, or Firm—Price, Gess & Ubell

[57] ABSTRACT

An improved electrode assembly of a modular configuration for sensing ion concentration includes a substrate mounted in a housing and being sandwiched by a first and second support layer of non-conductive material. A gelatinized solution is positioned in an opening between the first support layer and a substrate, while a second gelatinized solution is positioned in an opening between a second support layer and a substrate. Electric leads and electrodes are appropriately positioned on the substrate for operative contact with the respective gelatinized solutions. An ion-responsive member contacts one gelatinized solution, while an acqueous junction member extends through the respective support layers and substrates to contact another gelatinized solution.

13 Claims, 5 Drawing Sheets

SHEET TYPE ELECTRODE FOR USE IN THE MEASUREMENT OF ION CONCENTRATIONS

BACKGROUND OF THE INVENTION

1. Field of the Invention

The present invention relates to a sheet type electrode for use in the measurement of ions, for example, in the measuring of an ion-concentration, such as pH.

2. Description of the Technical Background

Recently, an electrode for measuring an ion-concentration,, such as pH, has been formed in a sheet-like shape in order to miniaturize the construction of the electrode, reduce the cost of production and to improve its operation and maintenance.

FIG. 7(A) discloses an external appearance of a composite sheet type electrode for use in the measurement of pH as described in a Japanese patent application by the present applicant (Horiba, Ltd.) filed on Nov. 28, 1986, and FIG. 7(B) shows a section of the measuring electrode of FIG. 7(A). Referring now to both FIG. 7 (A) and FIG. 7(B), reference numeral 61 designates a substrate formed of a material having a sufficiently high electrical insulating property even when immersed in a solution containing electrolytes. Reference numeral 62 designates an electrode formed on an upper surface of the substrate 61, the electrode 62 being formed by subjecting it to an appointed pretreatment and then a silk screen printing with an Ag paste. A part of the electrode 62 is formed as an internal electrode coated with an electrode material, such as for example AgCl, and the remaining part of the electrode 62 is formed as a lead portion 64.

Reference numeral 65 designates a support layer provided with a through hole 66 at a place corresponding to the internal electrode 63 and formed of a material having a sufficiently high electrical insulating property even when immersed in a solution containing electrolytes, such as for example polyethylene terephthalate. The support layer 65 is formed on the substrate 61 while exposing the lead wire 64 at its circumference. and a gel-evaporation inhibitor, such as glycerine, to a basic internal solution prepared by adding a phosphoric acid-buffering agent to, for example, a 3.3 M-aqueous solution of KCl supersaturated with AgCl. The internal solution 67 is placed into the through hole 66 by heating it to turn it into a paste and then screen printing it so that its upper surface may project slightly over the upper surface of the support layer 65 in a free condition and also overlap on the internal electrode portion 63.

Reference numeral 68 designates a flat plate-like response membrane having its lower surface contacting an upper surface of the gelatinized internal solution 67. The gelatinized internal solution 67 is sealed in the through hole 66, and the membrane 68 is fixedly mounted on the support layer 65 along its circumference by the use of an adhesive material 69 (for example, organic high molecular adhesives of silicon-, epoxy-, urethane- and the like series containing silane coupling agents and the like).

Referring to FIG. 7(A), reference numeral 70 designates a liquid junction membrane formed of porous inorganic sintered materials or porous organic high molecular materials impregnated with KCl having its lower surface contacting an upper surface of the other gelatinized internal solution. The membrane 70 is adhered to an upper surface of the support layer 65 along its circumference. The internal construction of the liquid membrane portion 70 is nearly the same as that of the measuring electrode shown in FIG. 7(B). Reference numeral 71 designates a holder portion to retain a sample solution under test.

With the above described construction, for example in a measuring electrode assembly, the response membrane 68, the internal electrode portion 63 and the lead portions 64 are all formed on the same surface of the substrate 61 so that the following disadvantages may occur. For example, the sample solution can run over the holder portion 71 or the sample solution can be inadvertently dropped. As a result, the sample solution can adhere to the lead portions 64, whereby a poor insulation can occur in the lead portions 64. When the response membrane 68 is permeable to light, a further disadvantage occurs in that an outside light is directly incident upon the internal electrode portion 63, whereby the measurement is influenced by the light.

Also, a reference electrode assembly can have similar problems.

SUMMARY OF THE INVENTION

The present invention was achieved in view of the above described matters to provide a sheet type electrode assembly, for use in the measurement of ions, capable of accurately carrying out the measurement without developing any poor insulation problem and preventing any influence by a light.

In order to achieve the above described object, a sheet type electrode assembly, for use in the measurement of ions according to the present invention, is characterized by a first support layer, formed of a material having a sufficiently high electrical insulating property, which is positioned on an upper surface of a substrate also having a sufficiently high electrical insulating property. Electrodes are provided with an internal electrode portion and lead portions being adhered to a lower surface of the substrate. A second support layer is formed of a material having a sufficiently high electrical insulating property on the lower surface of the substrate while still exposing the lead portions.

In the present invention a selective ion-response membrane or a liquid junction portion can contact a sample solution on an upper surface side of a substrate formed of a material having a sufficiently high electrical insulating property. Internal electrode portions and lead portions are formed on a lower surface side of the substrate, so that the insulating characteristics of the substrate can be sufficiently utilized and insulation problems in the lead portions due to sample spills and the like can be prevented from occurring.

In addition, even in the case where an ion-response membrane of a measuring electrode could be permeable to a light, the outside light is cut off by the substrate so that light can be prevented from being directly incident upon the internal electrode portion.

BRIEF DESCRIPTION OF THE DRAWINGS

A preferred embodiment is shown in FIGS. 1 to 4, in which.

DESCRIPTION OF THE PREFERRED EMBODIMENTS

Figure 1:
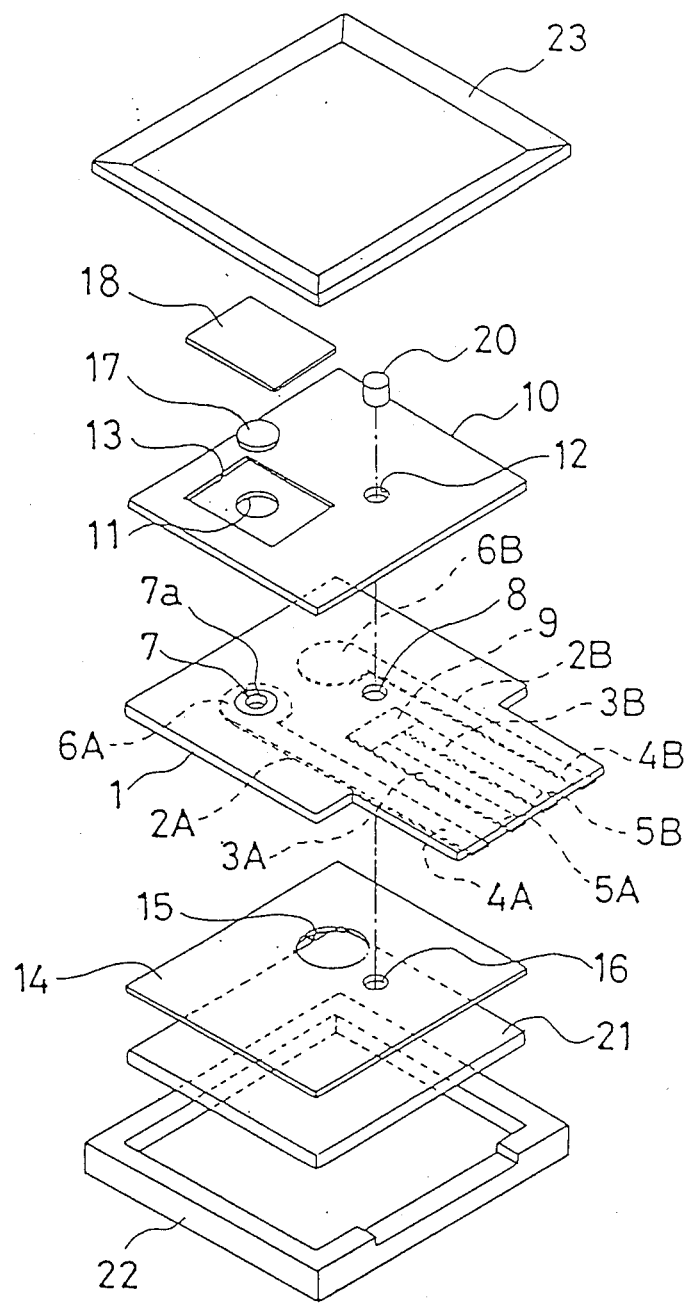
FIG. 1 is an exploded perspective view, showing a sheet type electrode assembly for use in the measurement of pH to which the present invention is applied.
Figure 2:
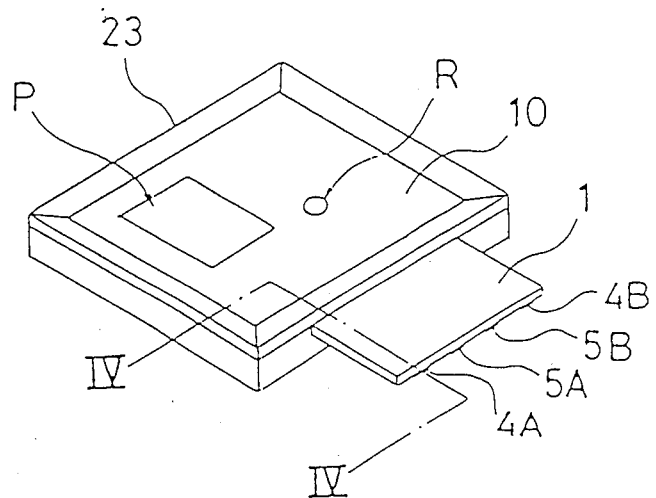
FIG. 2 is a perspective view showing an external appearance of the sheet type electrode of FIG. 1.

The preferred embodiments of the present invention are below described with reference to the drawings. A sheet type composite electrode for use in the measurement of pH is described.

Referring now to FIGS. 1 to 4, reference numeral 1 designates a non-conducting substrate (in this preferred embodiment a polyethylene terephthalate plate) formed of a material having a sufficiently high electrical insulating property even when immersed in a solution containing electrolytes. Examples of applicable organic high molecular materials are polyethylene, polypropylene, polyethylene terephthalate, acryl and polyfluoroethylene, and inorganic materials, such as silica glass and pyrex.

Two pairs (an inside pair and an outside pair) of electrodes 2A, 2B, and 3A, 3B are adhesively formed on a lower surface of the substrate 1 by adhering a metal selected from a group consisting of electrically conductive Ag, Cu, Au, Pt and the like and alloys thereof, a paste containing said metal or a semiconductor, such as $IrO_2$ and $SnO_2$, to the lower surface of the substrate 1 by physical plating methods, such as vacuum vapor deposition and CVD, chemical plating methods, such as electrolysis method and non-electrolysis method, or printing methods, such as silk screen method, anastatic printing method and flat plate method (in this preferred embodiment the lower surface of the substrate 1 is subjected to the grafting process and the anchoring process with a silane coupling agent and the like, and then an Ag paste is silk screened).

A base end portion can be positioned at one extended end edge portion of the substrate 1, for each of the electrodes 2A, 2B, 3A, 3B and formed as a lead portion 4A, 4B, 5A, 5B. The other nearly circular pad portion can be positioned at a nearly central portion of the substrate 1 in the outside pair of electrodes 2A, 2B to be formed as internal electrode portions 6A, 6B coated with an electrode material, such as AgCl, (by physical plating methods, chemical plating methods or printing methods in the same manner as in the above mentioned). One internal electrode portion 6A (pH-measuring electrode side P) is provided with an aperture or through hole 7, with an internal surface subjected to an electrically conducting treatment, at a nearly central portion thereof while the other internal electrode portion 6B (reference electrode side R) is provided with a through hole 8 formed adjacent thereto. Reference numeral 7a designates an electrically conductive portion in the through hole 7. In addition, a temperature compensating electrode portion 9, such as thermistor, is formed between the other pointed end portions so as to be positioned at a nearly central portion of the substrate 1 in the inside pair of electrodes 3A, 3B.

Reference numeral 10 designates a first support layer positioned on an upper surface of the substrate 1 and formed of a material having a sufficiently high insulating property (in this preferred embodiment, a polyethylene terephthalate layer) in the same manner as the substrate 1 and provide with through holes 11, 12 formed at a place corresponding to the through hole 7 passing through the internal electrode portion 6A formed in the substrate 1 and the through hole 8 formed adjacent to the other internal electrode portion 6B, respectively. A recessed or concaved portion 13 is formed on the upper surface side of the substrate 1 so as to extend around the through hole 11.

The first support layer 10 is formed by a screen printing method or a heat melt method in which adhesives are used for securing a sufficiently high electrical insulating material (for example 10 M$\Omega$ or more, for example, polyolefine series, silicon resin series and the like). In addition, the upper surface of the support layer 10 is subjected to a grafting process and anchoring process with a silane coupling agent and the like.

Reference numeral 14 designates a second support layer formed on a lower surface of the substrate 1 and formed of a material having a sufficiently high electrical insulating property (in this preferred embodiment a polyethylene terephthalate layer) in the same manner as substrate 1 and the first support layer 10. The second support layer is provided with through holes 15 and 16 which are formed at places corresponding to the other internal electrode portion 6B and the through hole 8 formed in the substrate 1, respectively. This second support layer 14 is formed by the same method as used with the first support layer 10.

Reference numeral 17 designates a gelatinized internal solution positioned in the through hole 11 of the support layer 10 formed by adding a gelatinizer (such as agar-agar, gelatine, glue, alginic acid and various kinds of hygroscopic acrylic polymer) and a gel-evaporation inhibitor (such as glycerine and ethylene glycol) to a basic internal solution comprising a 3.3 M-aqueous solution of KCl supersaturated with AgCl and containing a phosphoric acid-buffer solution. This mixture can be molded into a disc-like shape, as shown in FIG. 1.

Gelatinized internal solution 17 can be charged into the through hole 11 by, for example, heating to turn it into a paste and then printing the paste by a screen printing method so that an upper surface thereof may slightly project over the upper surface of the first support layer 10 in a free condition. The internal solution 17 is sealed up tightly in the through hole 11 and connected to the internal electrode portion 6A through the electrically conductive portion of the through hole 7 by providing the flat plate-like selective ion-response membrane 18 of an appointed size so that its lower surface may be closely brought into contact with an upper surface of the gelatinized solution 17.

Figure 3:
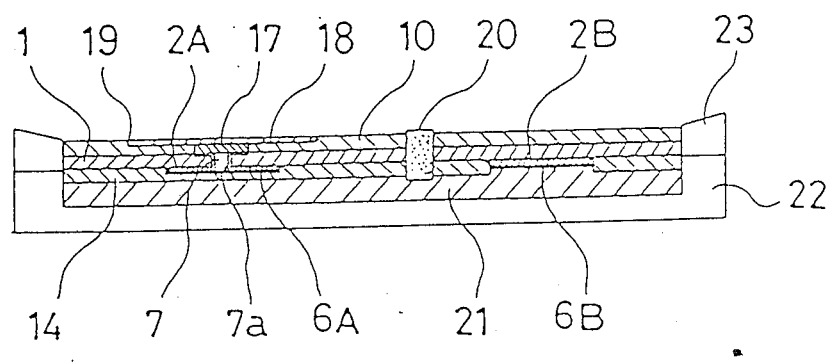
FIG. 3 is a partially developed sectional view.
Figure 4:
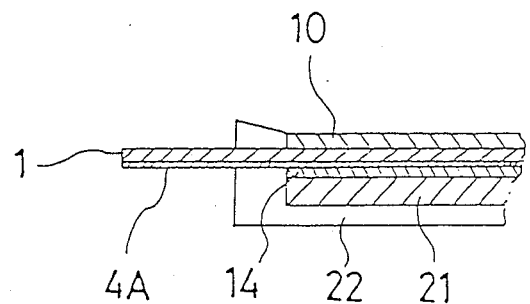
FIG. 4 is a sectional view of FIG. 2 taken along a line IV—IV thereof.

Reference numeral 19 in FIG. 3 designates adhesives having a sufficiently high electrical insulating property for fixedly mounting the response membrane 18 on the first support layer 10 along a circumference thereof. High molecular adhesives of silicone series, epoxy series, urethane series and the like containing a silane coupling agent and the like can be used as the adhesives.

Reference numeral 20 designates a gel-impregnated hydrophilic high molecular porous substance charged so as to pass through the through holes 12, 8, 16 which are formed at a place corresponding to the first support layer 10, the substrate 1 and the second support layer 14, respectively. The gel-impregnated hydrophilic high molecular porous substance 20 is obtained by impregnating a hydrophilic high molecular porous substance, such as a sintered chemically stabilized hydrophilic high molecular particle material. For example, a sintered body of an olefine series high polymer powdery material having a mechanical strength of the same degree as that of polyolefine and a hydrophilic property given by a denaturation treatment (for example, a Sunfine AQ [trade name] manufactured by Asahi Kasei Co., Ltd.), can be impregnated with a gelatinized composite without drying out, that is to say by depositing KCl and without losing its wetness characteristic from the surface of the porous substance even when left unattended in air, such as a U-jelly (trade name) manufactured by Showa Denko Co., Ltd. belonging to a water-contained jelly mainly comprising a sodium salt of acrylic polymer. The gel-impregnated hydrophilic high molecular porous substance 20 is located so as to slightly project over the surface of the first support layer 10 and can serve as a liquid junction portion of the reference electrode.

Reference numeral 21 designates a gelatinized internal solution pad having a chemical composition which is the same as that of the above described gelatinized internal solution 17. The internal solution pad is brought into contact with not only the internal electrode portion 6B, through the through hole 15, but also the gelatinized hydrophilic high molecular porous substance 20 through the hole 16.

Reference numeral 22 designates a bottom housing case. Reference numeral 23 designates an upper housing case that is a holder of a solution to be tested and which extends around the first support layer 10.

With the above described construction, the selective ion-response membrane 18 is formed on the upper surface of a substrate 1 which is a material having a sufficiently high electrical insulating property. Membrane 18 connects with the internal electrode portion 6A formed on the lower surface of the substrate 1 through the gelatinized internal solution 17 and the electrically conductive portion 7a of the through hole 7 formed in the substrate 1. The gel-impregnated hydrophilic high molecular porous substance 20 formed on the upper surface side of the substrate is connected with the internal electrode portion 6B formed on the lower surface side of the substrate 1 through the gelatinized internal solution 21, whereby the appointed measurement of pH can be carried out.

The substrate 1 is provided with the internal electrode portions 6A, 6B and the lead portions 4A, 4B, 5A, 5B formed on its lower surface side thereof so that the above described insulation characteristics of the substrate 1 can be sufficiently utilized and a breakdown in the insulation characteristics for the lead portions 4A, 4B, 5A, 5B due to any spill of a testing subject and the like can be prevented from occurring.

In addition, even though the selective ion-response membrane 18 is optically transparent, outside light is cut off by the opaque substrate 1 so that light is prevented from being directly incident upon the internal electrode portion 6A, whereby accurate measurement can be achieved.

Figure 5:
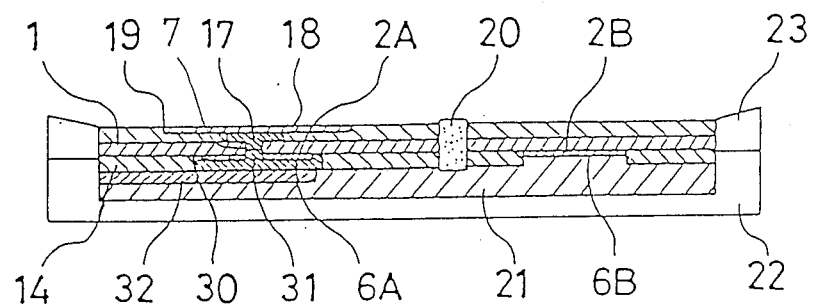
FIG. 5 is a sectional view showing another preferred embodiment of the present invention.

Although in the above-described preferred embodiment the electrically conductive portion 7a is formed in a through hole 7 formed in the substrate 1, a through hole 30 may also be formed at a position corresponding to the internal electrode portion 6A in the second support layer 14 so as to communicate with the through hole 7 and to fill also the inside of the through hole 30 with a gelatinized internal solution 31 having the same composition as that of the gelatinized internal solution 17, as shown in FIG. 5. Referring to FIG. 5, reference numeral 32 designates a third support layer for dividing the gelatinized internal solution 21 from the gelatinized internal solution 31 so that they are not brought into contact with each other. The third support layer 32 is formed in the same manner as the first support layer 10 and the second support layer 14.

With the above-described construction, the selective ion-response membrane 18 formed on the upper surface side of the substrate 1 is connected with the internal electrode portion 6A formed on the lower surface side of the substrate 1 through the gelatinized internal solution 17 and the gelatinized internal solution 31.

Figure 6:
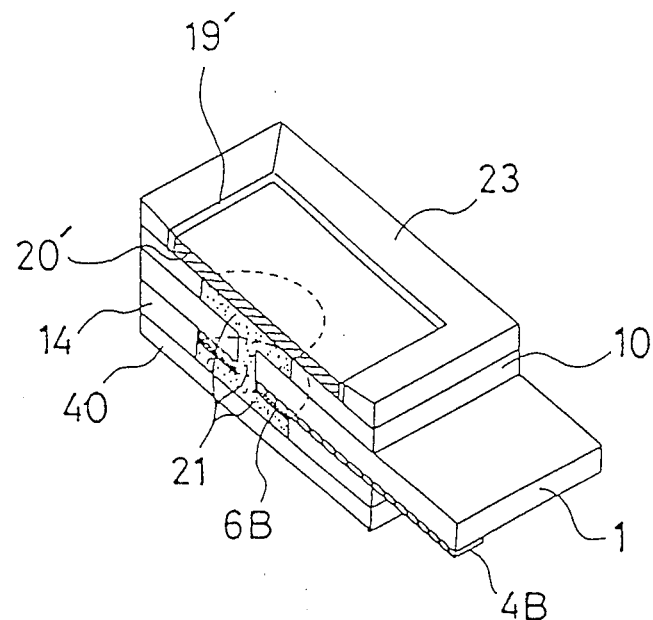
FIG. 6 is a partially broken perspective view showing another preferred embodiment of the present invention.
Figure 7A:
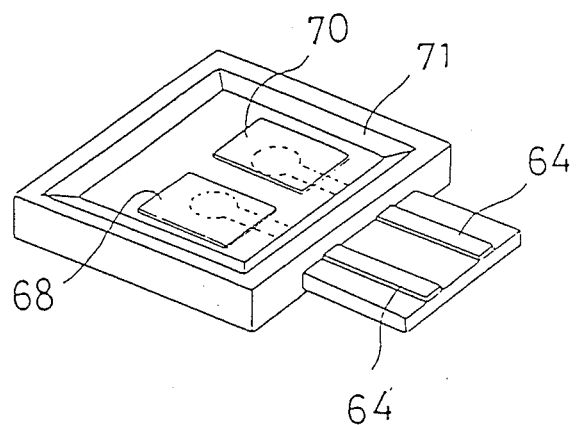
FIG. 7(A) and FIG. 7(B) are a perspective view for describing the technical background, respectively.
Figure 7B:
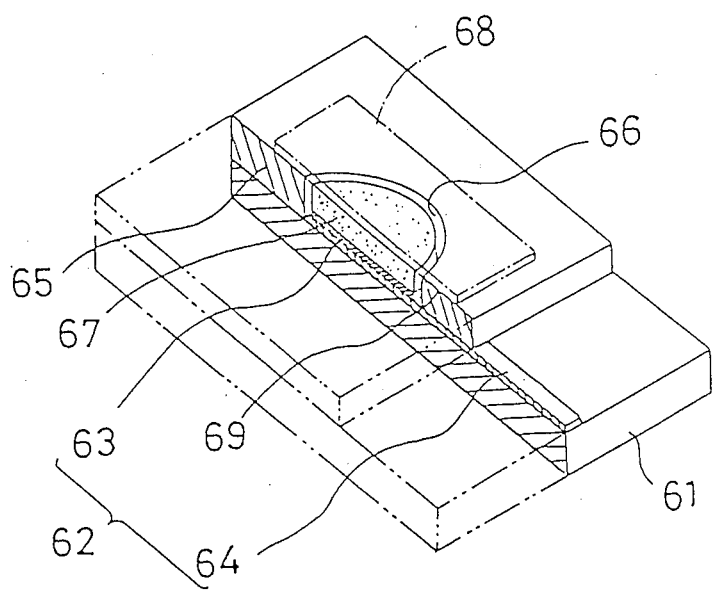

In addition, a reference electrode having such a construction as shown in FIG. 6 may be used. That is, referring to FIG. 6, reference numeral 20' designates a liquid junction membrane formed of an inorganic sintered porous substance or an organic high molecular porous substance impregnated with KCl joined to the first support layer 10 and the sample-solution holder 23 through an adhesive material 19' having a high electrical insulating property along a circumference thereof so that its lower surface may be contacted to the upper surface of the gelatinized internal solution 21. In addition, reference numeral 40 designates a third support layer formed of, for example, the same material as the first support layer 10. The same constituent members in FIG. 6 as in FIG. 1 are designated by the same reference numerals as in FIG. 1 and their description is hereby omitted.

The present invention can be applied to various kinds of measuring electrodes (glass electrode) and reference electrodes as well as a composite electrode for use in a measurement comprising both electrodes in combination or in addition to the above described sheet type measuring electrode for use in the measurement of pH.

As described, a sheet type electrode for use in the measurement of pH according to the present invention includes a first support layer formed of a material having a sufficiently high electrical insulating property positioned on an upper surface of a substrate having a sufficiently high electrical insulating property. An electrode, with internal electrode portions and lead portions, is adhered to a lower surface of the substrate. A second support layer of a material having a sufficiently high electrical insulating property is formed on the lower surface of the substrate with the lead portions exposed, so that any poor insulation characteristics due to an operation mistake can be prevented and accurate measurement can be achieved without being influenced by light.

The specification above describes only certain preferred embodiments of the present invention, and it is contemplated that various modifications to the above can be effected but nevertheless come within the scope of the present invention as defined by the claims.

What is claimed is:

1. In a sheet-configured electrode for use in the measurement of ion concentrations, the improvement comprising:
   a substrate of a non-conducting material defining a throughhole;
   an electrode assembly having a glass electrode disposed side by side to a reference electrode, each electrode having a different internal construction from the other, the glass electrode being provided with an internal electrode portion directly aligned with said throughhole and a lead portion, said portions being adhered to a lower surface of the substrate, the lower surface being opposite a side of the substrate from which a sample is received by the sheet-configured electrode, and a support layer of non-conducting material formed over a portion of the electrode assembly while exposing the lead portion.

2. The invention of claim 1 wherein another support layer of a non-conducting material is positioned on the upper surface of the substrate.

3. The invention of claim 2 further including a selective ion-responsive membrane of the glass electrode on the other support layer, the other support layer having a throughhole aligned with the throughhole of the substrate, the ion-responsive membrane being positioned over the aligned throughholes.

4. The invention of claim 3 wherein a gelatinized internal solution is positioned in the throughhole in the other support layer.

5. An improved structure for sensing ion-concentration comprising:

a housing member;

a substrate mounted in the housing member;

a first support layer of a non-conductive material positioned directly over the substrate;

a second support layer of a non-conductive material positioned below the substrate, the substrate, first support layer and second support layer having appropriately positioned openings to define a conduit among them;

a first gelatinized solution communicating through openings between the first support layer and the substrate;

a second gelatinized solution communicating through openings between the second support layer and the substrate;

an ion-responsive membrane positioned across the first gelatinized solution and above the first support layer;

means providing an electrical lead portion and an internal electrode portion on a bottom portion of the substrate for operative contact with the first and second gelatinized solutions, the lead portion extending outside of the housing, and an aqueous junction member extending through openings in the first support layer, second support layer, and the substrate.

6. The invention of claim 5 wherein the first gelatinized solution is mounted in an opening in the first support layer.

7. The invention of claim 5 wherein said internal electrode portion is mounted on the lower surface of the substrate and extends into an opening in the second support layer for contact with the second gelatinized solution.

8. The invention of claim 5 wherein the aqueous junction member is a porous sintered plug member that extends from a surface of the first support layer through the substrate and the second support layer to contact the second gelatinized solution.

9. The invention of claim 5 wherein the substrate, support layers and gelatinized solutions are formed in a sheet-like construction.

10. The invention of claim 5 wherein the substrate is opaque to incident light.

11. In an improved sheet-configured structure having an electrode assembly on a bottom surface of a substrate, said electrode assembly having a sensing electrode including an internal electrode portion and a lead portion, said structure receiving a sample from above a top surface of the substrate, the substrate having a throughhole therein, wherein the improvement comprises:

said substrate having an end edge portion on which said lead portion is disposed, and also having a central portion;

a first support layer directly interfacing said top surface such that said end edge portion remains exposed, said first support layer having a first throughhole therein for communication between said sample and said electrode assembly, said first throughhole being directly aligned with said substrate throughhole; and a second support layer directly interfacing said bottom surface and having a second throughhole therein such that said second support layer covers said central portion while leaving said end edge portion exposed.

12. The improvement of claim 11 further including an internal solution layer directly interfacing said second support layer from a side opposite to that on which said electrode assembly is located.

13. The improvement of claim 12 further including an internal solution element fixed in said first throughhole.

* * * * *